Figure 1:
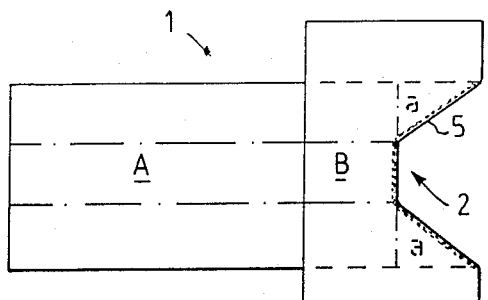

United States Patent [19]

Hanssen

[11] Patent Number: 4,889,136
[45] Date of Patent: Dec. 26, 1989

[54] SURGICAL DRAPE AND A METHOD FOR ITS MANUFACTURE

[75] Inventor: Carl-Otto Hanssen, Kullavik, Sweden

[73] Assignee: Molnlycke AB, Gothenburg, Sweden

[21] Appl. No.: 201,276

[22] Filed: May 23, 1988

[30] Foreign Application Priority Data

Jun. 16, 1987 [SE] Sweden ............................... 8702508

[51] Int. Cl.⁴ ............................................. A61B 19/08
[52] U.S. Cl. .................................... 128/855; 128/853; 128/849
[58] Field of Search ....................... 128/849, 853, 855

[56] References Cited

U.S. PATENT DOCUMENTS

| | | | |
|---|---|---|---|
| 3,856,005 | 12/1974 | Sislian | 128/849 |
| 4,040,418 | 8/1977 | Collins | 128/852 |
| 4,586,498 | 5/1986 | Morris | 128/853 |

FOREIGN PATENT DOCUMENTS 0140858 5/1985 European Pat. Off. .
8305946-9 7/1985 Sweden .

*Primary Examiner*—Robert A. Hafer
*Assistant Examiner*—Kevin G. Rooney
*Attorney, Agent, or Firm*—Young & Thompson

[57] ABSTRACT

The present invention relates to a surgical drape having a first rectangular part (A) which is intended to cover a patient and a second rectangular part (B) which is joined to the first drape part (A) and which is intended to be placed over an anaesthetist's arch. In accordance with the invention, one short side of the first drape part has formed therein a cut-out (2) in the shape of a truncated V. The second drape part (B) has formed therein a similar cut-out (2), which is formed in the center of one long side of the second drape part. The first and second drape parts are joined together along the edges of the cut-outs. The invention provides a surgical drape which can be easily manufactured by machine and which is easily managed.

10 Claims, 2 Drawing Sheets

SURGICAL DRAPE AND A METHOD FOR ITS MANUFACTURE

The present invention relates to a surgical drape which has a first rectangular part for covering a patient, and a second rectangular part which is intended to cover an anaesthetist's arch or stand. The invention also relates to a method for producing such a surgical drape.

When performing surgery, it has been found problematic hitherto to screen the anaesthetist and his personnel from the surgical area in a simple and satisfactory manner. As an auxiliary means of establishing a screen between the anaesthetist and the surgical area there is used an anaesthetist's arch or stand, which is substantially higher than the operating table and extends transversely across the table, and which is intended to support part of the surgical drape in a manner to form a vertical screening wall. The screen forming part of the drape is connected to the remainder of the drape, which is intended to cover the operating table and the patient lying thereon, and also to hang down from the table.

It is impracticable to use simply a surgical drape which consists of an elongated single length, due to the problems created by such a drape in the transition region or juncture between the drape part which covers the operating table and the drape part which is placed over the anaesthetist's arch. This arch extends laterally beyond the sides of the operating table, so that those parts of the drape which hang outside the edges of the table in the vicinity of the arch will not hang vertically downwards, but instead project laterally from said table edges, due to continuation of the drape over the arch. These laterally projecting drape portions render difficult surgery that is performed in the region of the anaesthetist's arch, for instance chest operations. However, a single piece surgical drape is previously known from our Swedish Patent Specification No. 8305946-9, which discloses a particularly configured transition portion between said drape parts, which solves the aforesaid problems.

Instead of a single length surgical drape there can be used a drape which consists of two separate parts, a first elongated part which is intended to cover the operating table, and a second elongated part which is oriented transversely to the first drape part and which is intended to form a vertical screen in the vicinity of the anaesthetist's arch, these drape parts being joined solely in the region which extends across the width of the operating table. However, although those portions of the first drape part located on the sides of the table will hang down vertically therefrom, even in the vicinity of the anaesthetist's arch, this kind of drape arrangement is also encumbered with serious drawbacks, since no vertical screen is obtained externally of the table, downwardly from the level of the upper surface of the table.

There are available commercially surgical drapes which are provided with additional drape parts for forming a vertical screen on the sides of the anaesthetist's arch up to the level of the arch, these drape parts being connected to the transverse anaesthetist part. These additional drape parts are also joined to those side portions of the drape which hang down from the operating table when the drape is in use, so as to form a totally impervious screening wall. Although a good screening effect can be obtained on the sides of the operating table with drape arrangements of this kind, the manufacture of such drapes is particularly complicated and is probably only capable of being carried out manually. Such drape arrangements are now no longer produced, probably because of their high manufacturing costs.

The present invention, on the other hand, provides a surgical drape which can be manufactured easily by machine and with which the aforesaid drawbacks of prior art drapes have been entirely eliminated.

In accordance with the invention, one short side of the first part of a surgical drape of the aforesaid kind has formed therein a cut-out in the shape of a truncated V. The one long side of the second drape part has a similar cut-out formed therein. The first and second drape parts are also joined together along respective edges of the cut-outs.

The invention also relates to a method having the characteristic features set forth in claim 9 and intended for producing the inventive surgical drape.

The inventive surgical drape can be produced on relatively simple machines. Furthermore, the configuration of the inventive drape enables a natural transition to be formed between the vertical screening walls of the first drape part and the vertical screening wall parts of the second drape part which extend perpendicularly to said screening walls and hang down below the edges of the table.

Figure 2:
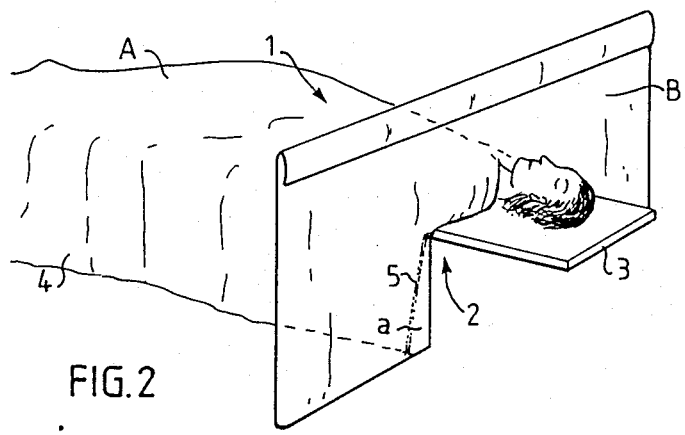
Figure 3:
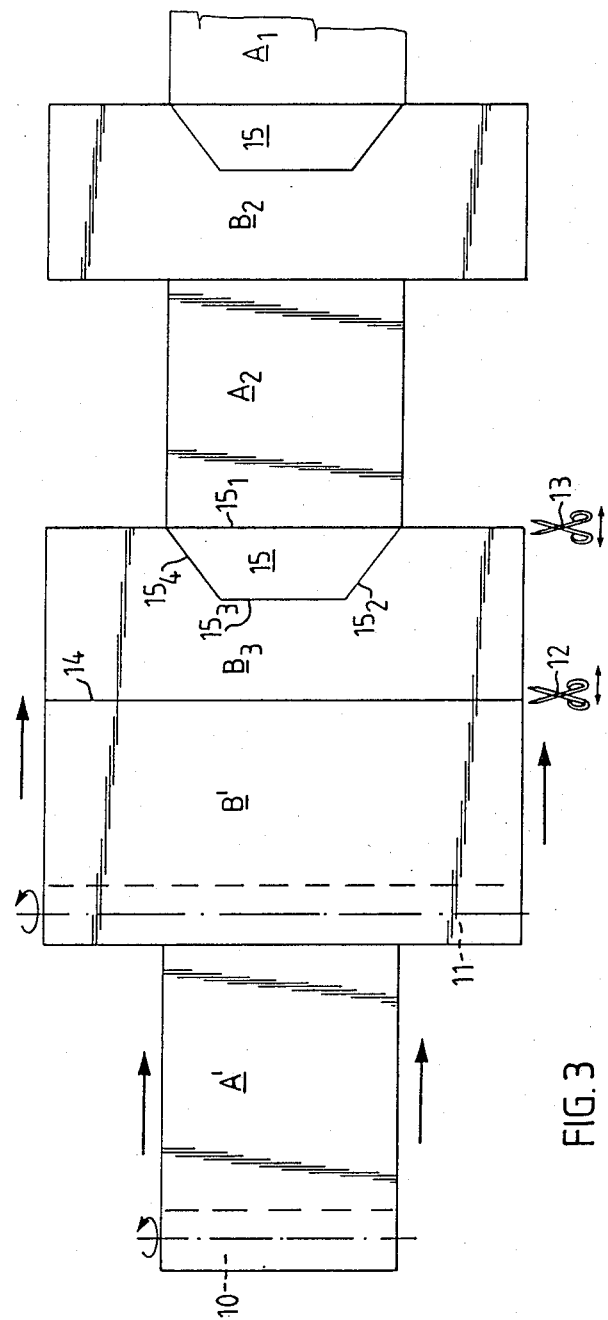

So that the invention will be more readily understood and further features thereof and advantages afforded thereby become more apparent, a preferred embodiment of the invention and a method for its manufacture will now be described in greater detail with reference to the accompanying drawings, in which FIG. 1 is a view from above of the inventive surgical drape in a flat state;

FIG. 2 is a schematic, perspective view of the drape of FIG. 1, with the drape in use; and FIG. 3 illustrates schematically a method of producing the drape of FIG. 1.

The surgical drape 1 illustrated in FIG. 1 has a first rectangular part A which is intended to cover a patient lying on an operating table and to form downwardly hanging, vertical screening walls on both sides of the table. A second rectangular part B is placed across the first drape part A, such as to form a T-shaped drape configururation and such that the right-hand short side of the first drape part A lies edge to edge with the right hand long side of the second drape part B, as seen in FIG. 1. The right-hand short side of the first drape part A has formed therein a cut-out 2 in the shape of a truncated V while a similar cut-out is provided in a corresponding part of the right-hand long side of the overlying second drape part B. The first and second drape parts A and B are joined together by a join 5 along edges of the cutouts in some suitable manner e.g. as by heat welding or gluing. The dimensions of the cut-outs 2 are preferably such that the base edges, i.e. the cut-out edges located between the two limbs of the V, have a length which corresponds to the standard width of an operating table, while the distance between the free ends of said limbs is equal to the width of the first drape part.

FIG. 2 is a schematic illustration of the surgical drape 1 in use, in which the first drape part A covers the body of a patient lying on an operating table 3 and forms depending vertical screening walls 4 on both sides of the table. The second drape part B is hung onto an anaesthetist's arch (not shown) and forms a transversely extending wall which screens the anaesthetist and the head of the patient from the surgical area. As illustrated in FIG. 2, parts of the second drape part B extend laterally beyond the operating table. As will be seen from FIG. 2, when the surgical drape is in use the flaps a of the first drape part, which lies longitudinally outside the base edge of the cut-outs 2 and is defined by the limbs of the cut-out and the longitudinal sides of the first drape part, are folded outwardly in the lateral direction. For the sake of illustration, the fold lines exhibited by the drape 1 when draped in use have been shown in chain lines.

As before mentioned, the length of the base edge of the cut-out 2 corresponds to the width of the operating table 3, so that when arranging the drape it can be draped naturally in the manner illustrated in FIG. 2. It will be understood in this regard that in order to enable those portions of the second drape part B which extend laterally beyond the base edge to hang downwardly on both sides of the operating table 3 freely and unhindered, the base edge should not be shorter than the width of the operating table. Furthermore, the base edge should be somewhat longer than the table width, since this edge does not lie flat across the table, but extends over the neck of a patient. There is no disadvantage, however, in making the base edge slightly longer than the optimum length since any additional length can be readily compensated for by displacing the side portions of the second drape part B in towards the center, until the corners between the base edge and the limbs of the cut-out are level with the edges of the operating table.

The first part A of the surgical drape 1 is made from a liquid absorbent, bacteria-impervious material. A suitable material in this regard is a two-layer or multilayer fiber-cloth/plastic film laminate. The second drape part B can be made of the same material as the first drape part, but is preferably made of a less expensive material, such as solely plastic film, since this part of the drape need not be capable of absorbing liquid. Furthermore, an advantage is afforded when the materials from which the two drape parts are made is thermoplastic, since this enables the drape part to be cut out and welded together in a single manufacturing stage.

FIG. 3 illustrates schematically the manufacture of a surgical drape according to the invention. Two material webs A', B' are fed from two rolls 10 and 11 parallel with one another in the direction indicated by arrows in FIG. 3, the material web A' in FIG. 3 extending beneath the material web B'. The material web A' is advanced continuously, whereas the web B' is advanced intermittently. Two clipping or punching devices 12, 13 are illustrated with the aid of scissors symbols in FIG. 3. The clipping, or shearing device 12 forms a cut 14 through the material web B' in a direction perpendicularly to the feed direction, whereas the clipping device 13 is constructed to cut out a piece 15 in the shape of an isosceles trapezoid with the cut-lines $15_1$–$15_4$ from the two material webs A', B'. The clipping devices are of the kind which have so-called flying shears which accompany the web feed movements as indicated by double arrows in FIG. 3.

Thus, the web B' moves to the right in the Figure during one step of the intermittent feed of said web while forming the cut-lines 14 and $15_1$–$15_4$ at the same time. The right-hand end of a surgical drape is therewith cut, as indicated by the reference $B_3$ in FIG. 3, at the same time as the material web A' is penetrated by the cut line $15_1$, thereby forming the left-and end of a preceding drapes $A_2$, $B_2$ in the manufacturing line. When the material webs A', B' consist of a thermoplastic material, the edges are also preferably welded together along the cut-lines $15_2$–$15_4$ at the same time as the isosceles trapezoid is cut out. Movement of the material web B' is interrupted when the web has been advanced through a distance which is equal to the distance between the cut lines 14 and $15_1$ and the knives of the clipping device have returned to their positions illustrated in FIG. 3. Since the web A' is advanced continuously, the web A' and the part $B_3$ of the material web B' connected thereto will continue to move to the right subsequent to halting the web B', and when the web B' is next advanced the part $B_3$ of said web will have taken the position at present occupied by the part $B_2$ in FIG. 3.

In accordance with one variant, the clipping device 13 may be arranged to cut the piece 15 solely along the center lines $15_2$–$15_4$. The piece of material 15 in the bottom web A' will therewith be extended, whereas the piece of material 15 in the top web B' will still constitute waste material.

The surgical drape according to the invention is preferably also provided with instrument pockets. These pockets are preferably manufactured by cutting the pieces of material 15 removed during manufacture into a suitable shape and gluing or welding said pieces to said drape parts along three pocket edges. The pocket openings, i.e. the non-glued or non-welded edges of the pockets, are also coated with a self-adhesive glue.

The invention thus provides a surgical drape which can be easily manufactured by machine and which is easy to manage. Furthermore, the first and second drape parts can be made, without limitation, from materials which satisfy the requirements placed on said drape parts, and the drape parts can be given mutually different lengths and widths.

I claim:

1. In a surgical drape comprising a first rectangular part (A) with two short sides and two long sides intended for covering a patient, and a second rectangular part (B) with two short sides and two long sides which is joined to the first part (A) and which is intended to be placed over an anaesthetist's arch, wherewith when the surgical drape is in use parts of the drape form substantially vertical screening walls (4) on both sides of an operating table (3), these walls extending along the sides of the first part (A) and being adapted to hang downwardly from both sides of the table to the second part (B) which is adapted to extend vertically upwards over the anaesthetist's arch; the improvement in which one short side of the first part (A) has formed therein a cut-out (2) having opposite sides that converge in a direction away from said one short side; the second part (B) having a cut-out (2) formed in one long side thereof, the latter cut-out having opposite sides that converge in a direction away from said one long side; the first and second drape parts (A, B) being joined together along the converging sides of the cut-outs.

2. A drape according to claim 1, in which said sides of the cut-out (2) slope towards the longitudinal extension of the first part (A) at an angle which is smaller than 50°.

3. A drape according to claim 1, in which the greatest width of the cut-out of said first part (A) is equal to the width of the first part (A).

4. A drape according to claim 1, in which the length of the least width of the cut-out (2) corresponds to the standard width of an operating table.

5. A drape according to claim 1, in which pockets are provided on parts of the drape.

6. A drape according to claim 1, in which the first part (A) is made of a liquid-absorbent, bacteria-impervious material.

7. A drape according to claim 6, in which the second part (B) is made of a material which is not liquid absorbent and which also is not impervious to bacteria.

8. A drape according to claim 6, in which the second part (B) is made of plastic film.

9. A drape according to claim 2, in which said angle is about 45°.

10. A drape according to claim 1, in which each said cut-out has the shape of a truncated V.

* * * * *